(12) United States Patent
Simpson

(10) Patent No.: US 7,572,007 B2
(45) Date of Patent: Aug. 11, 2009

(54) APODIZED DIFFRACTIVE IOL WITH FRUSTRATED DIFFRACTIVE REGION

(75) Inventor: Michael J. Simpson, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 11/497,594

(22) Filed: Aug. 2, 2006

(65) Prior Publication Data
US 2008/0030677 A1 Feb. 7, 2008

(51) Int. Cl.
G02C 7/06 (2006.01)
A61F 2/16 (2006.01)
G02C 7/04 (2006.01)
(52) U.S. Cl. ........................ 351/168; 351/161; 623/6.27
(58) Field of Classification Search .................. 351/159, 351/160 R, 161, 164, 168, 169, 171
See application file for complete search history.

(56) References Cited
U.S. PATENT DOCUMENTS 5,470,932 A 11/1995 Jinkerson
5,699,142 A 12/1997 Lee et al.
7,188,949 B2 * 3/2007 Bandhauer et al. .......... 351/168
2007/0182924 A1 * 8/2007 Hong et al. .................. 351/171

* cited by examiner

Primary Examiner—Darryl J Collins
(74) Attorney, Agent, or Firm—Armando Pastrana, Jr.

(57) ABSTRACT

In one aspect, the present invention provides a diffractive ophthalmic lens (e.g., a diffractive IOL) that includes an optic having an anterior surface and a posterior surface, where the optic provides a far focus. A frustrated diffractive structure comprising a plurality of diffractive zones is disposed on at least one of those surfaces so as to provide a near focus. Each zone is separated from an adjacent zone by a zone boundary that imparts an optical delay to the incident light. Further, at least two consecutive zone boundaries are configured such that a difference between their associated phase delays for at least one wavelength of the incident light is greater than about ¼ wavelength so as to direct a portion of the incident light to a location between the near and far foci.

19 Claims, 5 Drawing Sheets

US 7,572,007 B2

APODIZED DIFFRACTIVE IOL WITH FRUSTRATED DIFFRACTIVE REGION

BACKGROUND

The present invention relates generally to ophthalmic lenses, and more particularly, to intraocular lenses (IOLs) that provide enhanced intermediate vision.

Intraocular lenses are routinely implanted in patients' eyes during cataract surgery to replace the natural crystalline lens. Some IOLs employ diffractive structures to provide a patient with not only a far-focus power but also a near-focus power. Such IOLs may also provide a limited degree of intermediate vision due to the defocus properties of the two primary lens powers (i.e., the far and near powers).

There is, however, still a need for diffractive IOLs that can provide enhanced intermediate vision, and more particularly, there is a need for such IOLs that provide improved intermediate image quality without any significant degradation of the far and near vision.

SUMMARY

The present invention generally relates to diffractive ophthalmic lenses (e.g., diffractive IOLs) that provide near and far foci while directing a portion of the incident light to an intermediate location between the far and near foci. More particularly, such a diffractive lens can include a diffractive structure that is adapted to direct a portion of the incident light to the intermediate location. In many embodiments, the diversion of a portion of the incident light to the intermediate location is achieved by providing a sufficient difference between the phase delays generated by two or more zone boundaries of the diffractive structure.

In one aspect, the invention provides a diffractive ophthalmic lens (e.g., a diffractive IOL) that includes an optic having an anterior surface and a posterior surface, where the optic provides a far focus. A diffractive structure comprising a plurality of diffractive zones is disposed on at least one of those surfaces so as to provide a near focus. Each zone is separated from an adjacent zone by a zone boundary that imparts an optical phase delay to the incident light. Further, at least two consecutive zone boundaries (two zone boundaries separating one common diffraction zone from two different zones) are configured such that a difference between their associated phase delays for at least one wavelength of the incident light is greater than about $\tfrac{1}{20}$ wavelength $$\left(\tfrac{1}{20}\lambda\right),$$

and preferably greater than about $\tfrac{1}{4}$ wavelength $$\left(\tfrac{1}{4}\lambda\right),$$

e.g., in a range of about $\tfrac{1}{20}$ wavelength $$\left(\tfrac{1}{20}\lambda\right)$$

to about 1 wavelength $(1\lambda)$, so as to direct a portion of the incident light to a location between the near and far foci.

In a related aspect, the zone boundaries comprise a plurality of steps, where at least two consecutive steps exhibit a differential height adapted to provide a difference greater than about $\tfrac{1}{20}$ wavelength, and preferably greater than about $\tfrac{1}{4}$ wavelength, e.g., in a range of about $\tfrac{1}{20}$ wavelength to about 1 wavelength, in their associated phase delays.

In another aspect, in the above IOL having a plurality of steps as zone boundaries of its diffractive structure, a portion of the steps exhibit decreasing heights as a function of increasing distance from the center of the surface on which the diffractive structure is disposed, that is, a portion of the step heights are apodized.

In another aspect, the diffractive structure of the ophthalmic lens comprises a truncated diffractive structure that covers a portion, rather than the entirety, of a lens surface on which the structure is disposed.

In another aspect, in the above IOL, the two consecutive zone boundaries exhibit the aforementioned differential phase delays for at least one wavelength in a range of about 400 nm to about 700 nm (e.g., 550 nm).

In another aspect, the optic provides a far-focus optical power in a range of about 6 Diopters (D) to about 34 D. Further, the diffractive structure provides a near focus add power in a range of about 2 D to about 4 D, e.g., in a range of about 2.5 D to about 4 D or in a range of about 3 D to about 4 D. The effective add power of an IOL when implanted in the eye can be different from its nominal (actual) add power. For example, the combination of the corneal power and the separation between the cornea and the IOL can weaken the IOL's effective add power, e.g., a nominal 4 D add power can result in a 3 D effective add power for the whole eye. In the following sections, unless otherwise indicated, the recited values of add power refer to the nominal (actual) lens add power, which can be different from the effective add power when the IOL is implanted in the eye.

In a related aspect, the optic is formed of a biocompatible material. Some examples of such materials include, without limitation, soft acrylic, silicone, hydrogel, or other biocompatible polymeric materials having a requisite index of refraction for a particular application. For example, in some embodiments, the optic is formed of a cross-linked copolymer of 2-phenylethyl acrylate and 2-phenylethyl methacrylate commonly known as Acrysof.

In another aspect, in the above ophthalmic lens, at least one of the anterior or posterior surfaces includes a base profile that exhibits a selected degree of asphericity (e.g., one characterized by a conic constant in a range of about −10 to about −1000, e.g., in a range of about −10 to about −100) or toricity to provide improved image quality.

In another aspect, a diffractive ophthalmic lens is disclosed that includes an optic having an anterior surface, a posterior surface, and a diffractive structure comprising a plurality of diffractive zones disposed on at least one of those surfaces, where each zone is separated from an adjacent zone by a zone boundary. The optic provides a far focus corresponding to the zeroth diffraction order of the diffractive structure and a near focus corresponding to the first diffraction order of the structure. Further, the zone boundaries are characterized by a plurality of non-uniform step heights that provide non-uniform phase delays adapted to direct a portion of incident light to a location between the near and far foci so as to enhance intermediate vision.

In a related aspect, the non-uniform step heights comprise the heights of at least two consecutive steps each imparting a phase delay to the incident light such that a difference between those phase delays, for at least one wavelength of the incident light, is greater than about 1/20 wavelength $$\left(\frac{1}{20}\lambda\right)$$

(e.g., in a range of about 1/20 wavelength to about 1 wavelength).

In a related aspect, in the above diffractive lens, the optic provides a far-focus optical power in a range of about 6 D to about 34 D (e.g., in a range of about 16 D to about 28 D ) and a near focus add power in a range of about 2 D to about 4 D.

In another aspect, the diffractive zones are surrounded by a portion of the respective surface that lacks diffractive elements.

In other aspects, a diffractive ophthalmic lens (e.g., an IOL) is disclosed that comprises an optic having an anterior surface and a posterior surface, each of which is characterized by a base profile. The optic provides a far-focus optical power (e.g., in a range of about 6 D to about 34 D ), and includes a diffractive structure disposed on one of its surfaces that provides a near-focus optical power (e.g., in a range of about 2 D to about 4 D). The diffractive structure comprises a plurality of diffractive zones, at least two of which exhibit sufficiently different surface curvatures (e.g., a difference in a range of about 10% to about 50%) to cause a portion of the light incident on the optic to be directed to an intermediate location between the near and far foci for enhancing intermediate vision. For example, in some embodiments, the surface curvatures of at least two adjacent zones are sufficiently different to cause a portion of the incident light to be directed to the intermediate location.

In a related aspect, in the above ophthalmic lens, the surface curvature of at least one of the zones differs by more than about 20% (e.g., in a range of about 10% to about 50%) from the surface curvature(s) of one or more adjacent zones.

In another aspect, the invention provides a diffractive ophthalmic lens (e.g., an IOL) that provides an optic having an anterior surface and a posterior surface, where the optic provides a far focus (e.g., in a range of about 6 D to about 34 D ). A diffractive structure that comprises a plurality of diffractive zones is disposed on at least one of those surfaces to provide a near focus (e.g., one associated with an add power in a range of about 2 D to about 4 D). A surface of at least one of the diffractive zones exhibits an asphericity such that the diffractive structure directs at least a portion of the incident light to an intermediate location between the near and far foci. The asphericity can be characterized, for example, by a conic constant in a range of about −10 to about −1000, e.g., in a range of about −10 to about −100.

In another aspect, the locations of one or more zone boundaries (e.g., the radii of the zones relative to the optical axis) can be adjusted so as to direct a portion of the incident light to a location between the near and far foci. For example, the ophthalmic lens (e.g., an IOL) can include an optic having an anterior and a posterior optical surface, where the optic provides a far focus. A plurality of annular diffractive zones are disposed on one of those surfaces about an optical axis of the optic so as to provide a near focus, wherein each zone is separated from an adjacent zone by a zone boundary. At least one of the zones (i) has a boundary with a radial location relative to the optical axis that is defined by the following relation:

$$r_i^2 = r_0^2 + 2i\lambda f$$

wherein i denotes the zone number (i=0 denotes the central zone); λ denotes the design wavelength (e.g., in a range of about 400 nm to about 700 nm); f denotes a focal length of the near focus, and $r_0$ denotes the radius of the central zone. Further, at least another diffraction zone has a boundary with a radial location that differs sufficiently from that defined by the above relation for a putative respective zone so as to cause at least a portion of incident light to be directed to an intermediate location between the near and far foci. By way of example, the radial location of that another zone can differ from that defined by the above relation by a factor in a range of about 20% to about 50%.

In another aspect, a diffractive ophthalmic lens is disclosed that includes an optic having an anterior optical surface and a posterior optical surface, where the optic provides a far focus. A plurality of diffractive zones are disposed on at least one of those surfaces so as to provide a near focus. The diffractive zones comprise a central zone having a radius that is sufficiently different from $\sqrt{\lambda f}$, where λ denotes a design wavelength and f denotes a focal length of the near focus, such that at least a portion of incident light is directed to an intermediate location between the near and far foci.

In another aspect, in the above ophthalmic lenses, one or more optical surfaces can include a base profile exhibiting a selected degree of asphericity or toricity for providing enhanced vision quality.

Further understanding of the invention can be obtained by reference to the following detailed description in conjunction with the drawings, which are described briefly below.

DETAILED DESCRIPTION OF THE PREFERRED EMBODIMENTS

Figure 1A:
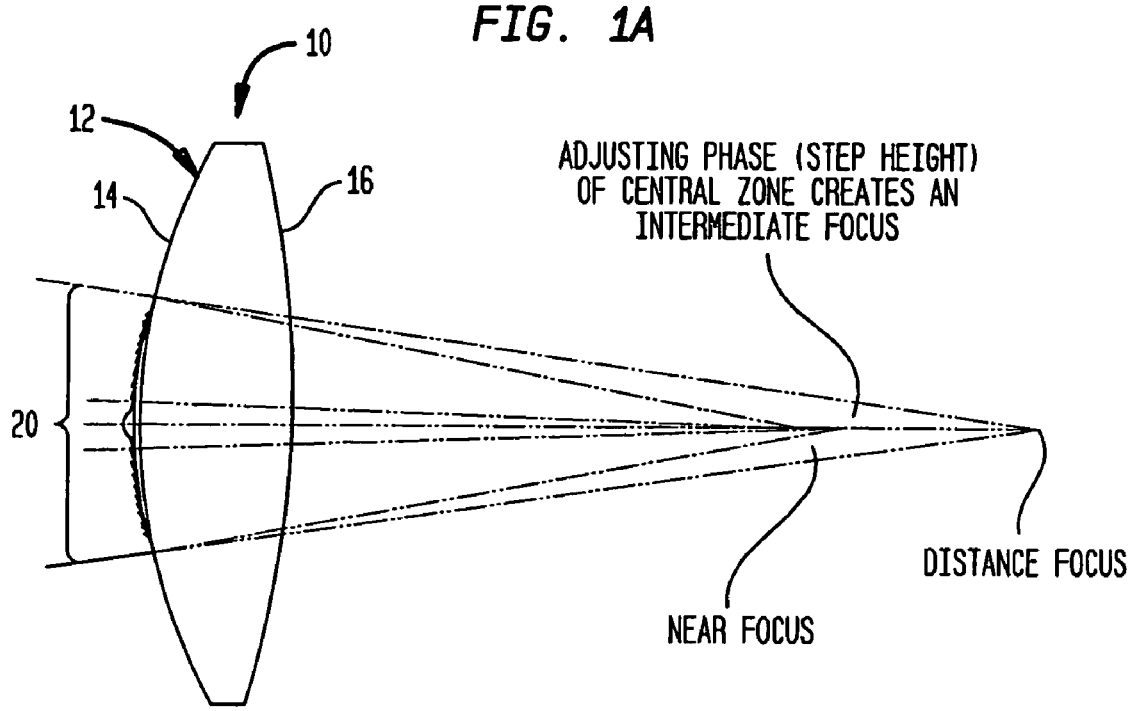
FIG. 1A is a schematic cross-sectional view of an IOL according to an exemplary embodiment of the invention.
Figure 1B:
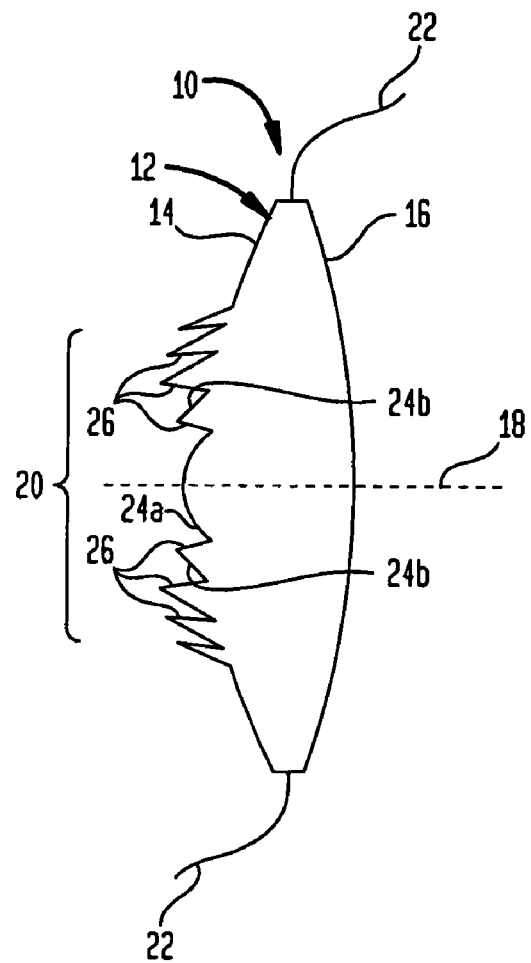
FIG. 1B is another cross-sectional view of an IOL according to an embodiment of the invention, illustrating a diffractive structure characterized by non-uniform step heights for directing a portion of incident light to an intermediate focus.

With reference to FIGS. 1A and 1B, an IOL 10 according to one embodiment of the invention includes an optic 12 having an anterior optical surface 14 and a posterior optical surface 16 disposed about an optical axis 18. While in this embodiment the optical surfaces 14 and 16 are generally convex so as to provide the IOL with a bi-convex shape, in other embodiments, the IOL can have other shapes, such as, plano-convex, plano-concave, or convex-concave. The curvatures of the anterior and posterior surfaces, together with the index of refraction of the material forming the lens, are selected such that the optic 10 provides a far focus optical power, e.g., in a range of about 6 Diopters (D) to about 34 D (e.g., in a range of about 16 D to about 28 D ). In some cases, the far-focus optical power of the lens can be in a range of about −5 D to about 5.5 D.

A diffractive structure 20, which is disposed on a portion of the anterior surface 14, provides a near focus with an add power, e.g., in a range of about 2 D to about 4 D (e.g., in a range of about 2.5 D to about 4 D or in a range of about 3 D to about 4D). The effective add power of the IOL when implanted in the eye can be different from its nominal (actual) add power. For example, the combination of the corneal power and the separation between the cornea and the IOL can weaken the IOL's effective add power, e.g., a nominal 4 D add power can result in a 3 D effective add power for the whole eye. In the following sections, unless otherwise indicated, the recited values of add power refer to the nominal (actual) add power of the lens, which can be different from the effective add power when the IOL is implanted in the eye.

The IOL 10 can further include a plurality of fixation members or haptics 22 that facilitate placing it in a patient's eye. The optic is preferably formed of a biocompatible material, such as soft acrylic, silicone, hydrogel or other biocompatible polymeric materials having a requisite index of refraction for a particular application. The haptics 22 can also be formed of suitable polymeric materials, such as polymethacrylate, polypropylene and the like. In some embodiments, the haptics 22 can be formed integrally with the optic 12 while in other embodiments; they can be formed separately and then coupled to the optic. In one embodiment, the optic 12 is formed of a cross-linked copolymer of 2-phenylethyl acrylate and 2-phenylethyl methacrylate, which is commonly known as Acrysof.

Figure 2:
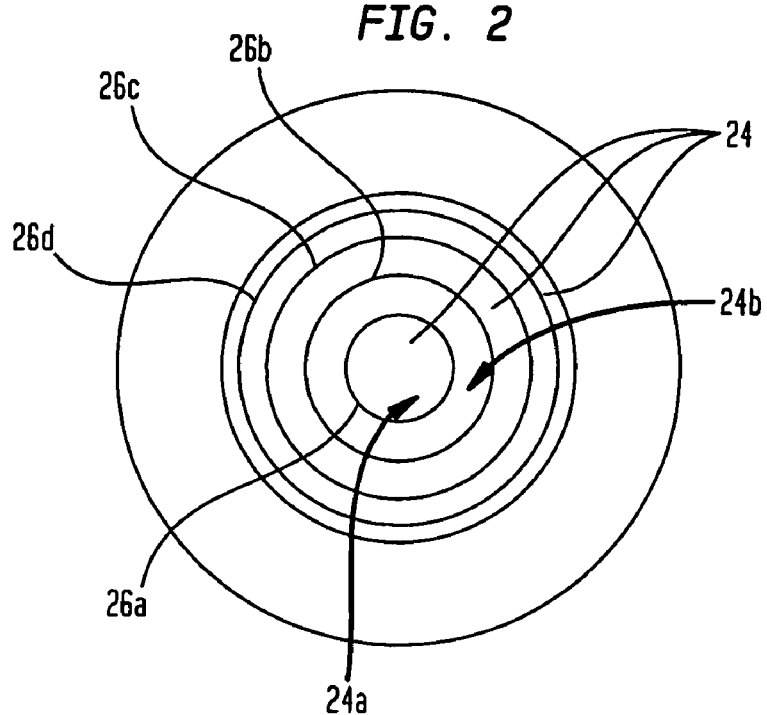
FIG. 2 is a schematic front view of the IOL of FIG. 1B illustrating a plurality of annular diffraction zones forming the diffractive structure.

Referring to FIGS. 1A, 1B and 2, the diffractive structure 20 is composed of a plurality of diffractive zones 24 separated from one another by a plurality of steps 26 (the step heights are exaggerated for clarity). More particularly, each zone is separated from an adjacent zone by a step (e.g., step 26a separating the first zone 24a from the second zone 24b) that imparts a phase delay to the incident light. As discussed further below, in this exemplary embodiment, a phase delay generated by the step 26a separating the central zone (the first zone) from the second zone is different from a phase delay caused by the other steps such that a portion of the light incident on the lens is directed to an intermediate location between the near and far foci.

In this exemplary embodiment, the diffractive zones comprise a plurality of annular zones whose boundaries are radially located relative to the optical axis 18 in accordance with the following relation:

$$r_i^2 = r_0^2 + 2i\lambda f \quad \text{Eq. (1)}$$

wherein i denotes the zone number (i=0 denotes the central zone), $\lambda$ denotes the design wavelength, f denotes a focal length of the near focus, and $r_0$ denotes the radius of the central zone.

In some embodiments, the design wavelength $\lambda$ is chosen to be 550 nm green light at the center of the visual response. Further, in some cases, the radius of the central zone ($r_0$) can be set to be $\sqrt{\lambda f}$.

As discussed in more detail below, in some other embodiments, the boundary location of one or more zones can deviate from that defined by the above relation so as to further facilitate directing a portion of the incident radiation to an intermediate location between the near and far foci.

As noted above, in this exemplary embodiment, the height of the step separating the first and the second diffraction zones is different from the heights of the other steps (which in this embodiment are substantially uniform) such that the diffractive structure directs a portion of the incident light to an intermediate location between the near and far foci. For example, the difference between the phase delay generated by the step 26a and that generated by each of the other steps (i.e., steps 26b-26d) can be greater than about 1/20 wavelength $$\left(\frac{1}{20}\lambda\right),$$

and preferably greater than about 1/4 wavelength $$\left(\frac{1}{4}\lambda\right),$$

for at least one wavelength of the incident light, e.g., for at least one wavelength in a range of about 400 nm to about 700 nm. By way of example, in one embodiment, the step heights can be defined in accordance with the following relation:

$$\text{Step height} = \frac{b\lambda}{(n_2 - n_1)} \quad \text{Eq. (2)}$$

wherein, b denotes the phase height, $\lambda$ denotes the design wavelength, e.g., 550 nm, $n_2$ denotes the refractive index of the optic, and $n_1$ denotes the refractive index of the medium surrounding the optic wherein, for the step 26a, b lies in a range of about −0.2 to about 0.2, and for the other steps, b lies in a range of about 0.45 to about 0.55, and is preferably about 0.5.

The above Eq. (2) indicates that the step height separating the central zone from its neighboring zone is different from the remaining step heights. More specifically, the step heights other than the one separating the central zone from its neighboring zone are substantially uniform and produce an optical phase delay that results in the diffractive structure dividing the incident light approximately equally between the near focus, which corresponds to the first order of the diffractive structure, and the distance focus, which corresponds to the zero$^{th}$ diffraction order. In contrast, the step height separating the central zone from its neighboring zone generates a different phase delay, which causes some of the incident light to be directed to an intermediate location between the near and far foci. In other words, the different phase delay generated by the step height between the central zone and its neighboring zone alters the contribution of the central zone to light diffracted by the diffractive structure such that while the central zone continues to contribute light to the near and far foci, it directs some of the light to an intermediate location between those foci—the central zone is not a perfect contributor to the regular diffractive structure. Such a diffractive structure is herein also referred to as a "frustrated diffractive structure" and the diffraction that it produces is also herein referred to as a "frustrated diffraction" to indicate that it modifies a regular diffraction pattern so as to divert some of the incident light to an intermediate location between the near and far foci. Further, the intermediate location is herein also referred to as the intermediate focus, although in many embodiments, the light convergence at the intermediate location does not result in as sharp a focus as those present in the near and far foci.

In some embodiments, the step separating the central zone from its neighboring zone is removed (that is, the step height between the first and second diffraction zones is set to zero) so as to direct a portion of the incident light to the intermediate location. In other words, the first and second diffraction zones are made into a single central zone for generating an intermediate focus.

Figure 3A:
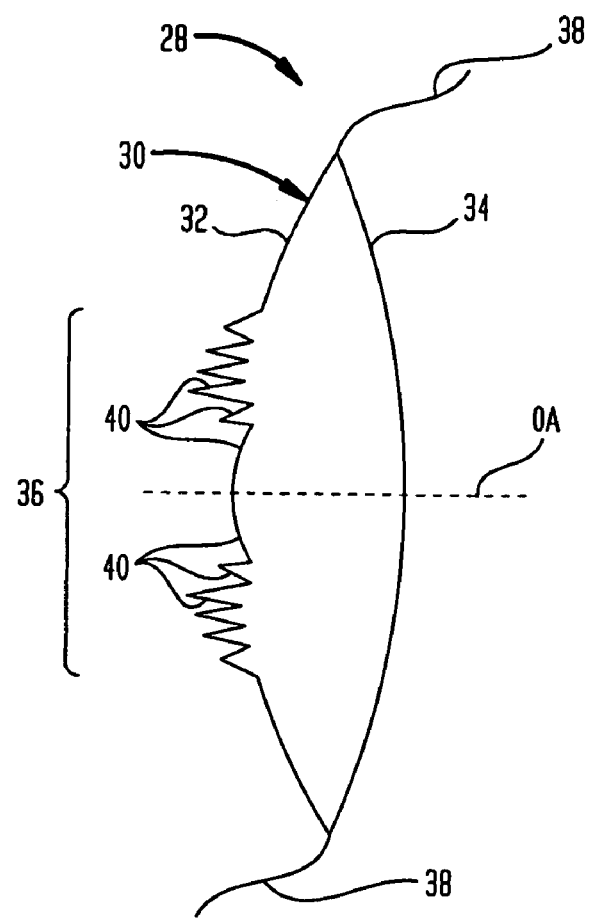
FIG. 3A is a schematic side view of a diffractive IOL according to another embodiment of the invention having an apodized diffractive structure.
Figure 3B:
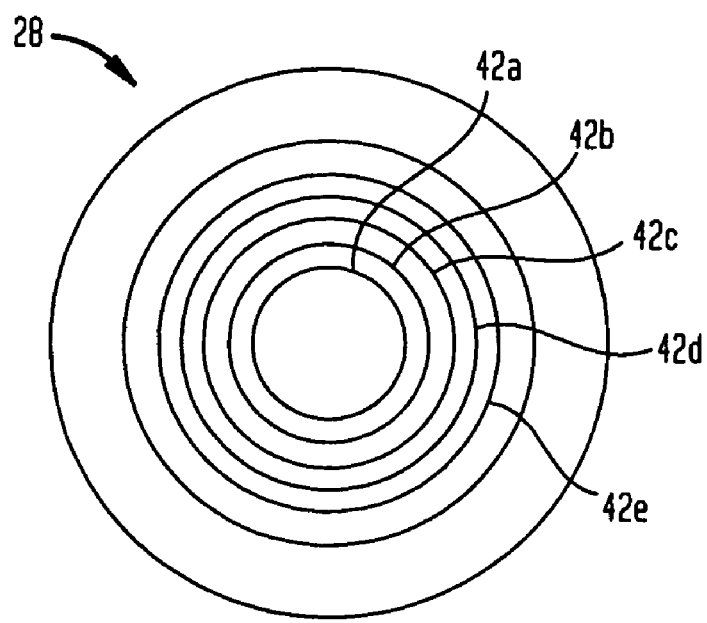
FIG. 3B is a schematic front view of the IOL of FIG. 3A.

In some embodiments, in addition to having at least two consecutive step heights generating phase delays that differ from one another by a value greater than a threshold (e.g., greater than about 1/20 wavelength), a plurality of the step heights separating the diffractive zones of the IOL's diffractive structure are apodized so as to shift the distribution of the light energy between the near and far foci as the pupil size changes, e.g., to reduce glare. By way of example, FIGS. 3A and 3B schematically depict an exemplary IOL 28 according to such an embodiment of the invention that includes an optic 30 having an anterior optical surface 32 and a posterior optical surface 34 disposed about an optical axis OA, and a diffractive structure 36 disposed on the anterior optical surface. Similar to the previous embodiment, the optic 30 provides a far-focus power, e.g., in a range of about 6 D to about 34 D (e.g., in a range of about 16 D to about 28 D). Further, the optic 30 includes haptics 38 that facilitate its implantation in a patient's eye.

The diffractive structure 36 is formed by a plurality of diffractive zones 40 separated from one another by a plurality of steps 42a-42e. Similar to the previous embodiment, the diffractive structure generates a near focus corresponding to its first diffraction order and a far focus corresponding to the zeroth order of the diffractive structure. Further, a difference between the phase delays generated by the consecutive steps 42a and 42b is configured, e.g., in a manner discussed above in connection with the previous embodiment, such that the diffractive structure directs a portion of the incident light to an intermediate location between the near and far foci. Further, in this embodiment, the heights of the steps 42b, 42c, 42d and 42e are apodized, i.e., they vary as a function of their radial distance from the optical axis OA. For example, in this exemplary embodiment, the heights of those steps decrease as their distances from the optical axis increase. This apodization causes a shift in the distribution of the light energy between the near and far foci as the pupil size varies, that is, as the number of zones contributing to the light diffraction changes.

With continued reference to FIGS. 3A and 3B, in this exemplary embodiment, the step heights of the zone boundaries of the diffractive structure 36 can be defined in accordance with the following relations:

for the step separating the central zone from the second zone (i.e., step 42a):

$$\text{Step height} = \frac{b\lambda}{(n_2 - n_1)} \quad \text{Eq. (4a)}$$

wherein
b is the phase height with a value in a range of about −0.2 to about 0.2 and the other parameters are defined below, and
for the other steps:

$$\text{Step height} = \frac{b\lambda}{(n_2 - n_1)} f_{apodize} \quad \text{Eq. (4b)}$$

wherein,
b denotes the phase height with a value between about 0.45 to about 0.55 (preferably about 0.5),
λ denotes the design wavelength, e.g., 550 nm,
$n_2$ denotes the refractive index of the optic,
$n_1$ denotes the refractive index of the medium surrounding the optic, and $f_{apodize}$ denotes an apodization function.

A variety of apodization functions can be employed. For example, in some embodiments, the apodization function ($f_{apodize}$) can be defined in accordance with the following relation:

$$f_{apodize} = 1 - \left\{ \frac{(r_i - r_{in})}{(r_{out} - r_{in})} \right\}^{\exp}, \; r_{in} \leq r_i \leq r_{out} \quad \text{Eq. (5)}$$

wherein
$r_i$ denotes the distance of each radial zone boundary from the intersection of the optical axis with the surface,
$r_{in}$ denotes the inner boundary of the apodization zone, which in the above exemplary embodiment corresponds to the inner boundary of the second diffraction zone,
$r_{out}$ denotes the outer boundary of the apodization zone, and
exp denotes an exponent to obtain a desired reduction in step heights. Further details regarding apodization of step heights can be found, e.g., in U.S. Pat. No. 5,600,142, which is herein incorporated by reference. Other apodization functions can also be employed. By way of example, alternative apodization functions disclosed in a co-pending patent application entitled "Truncated Diffractive Intraocular Lenses," which is assigned to the assignee of the present application, can be utilized.

Figure 4A:
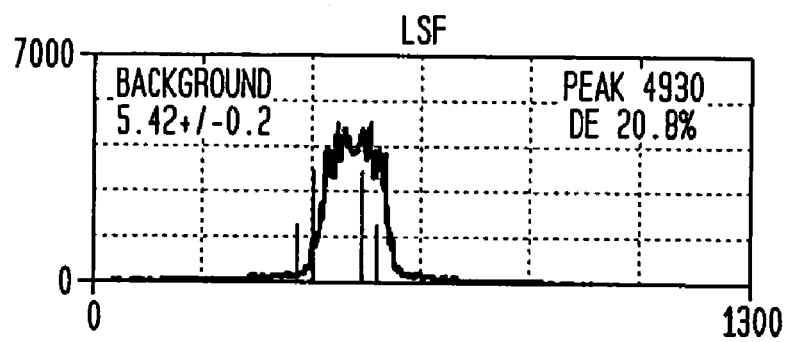
FIG. 4A is a theoretical line spread function (LSF) calculated at an intermediate focus for a conventional diffractive lens having an apodized diffractive structure.
Figure 4B:
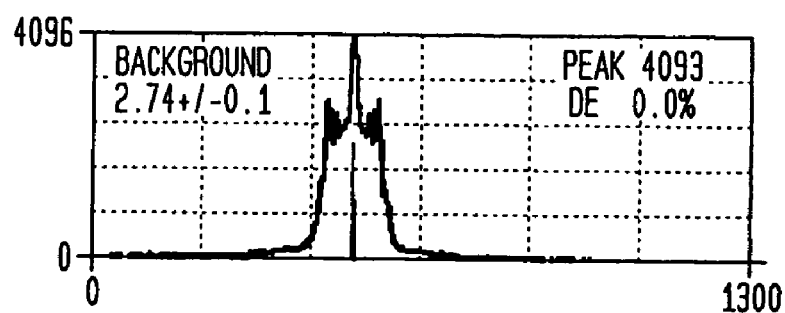
FIG. 4B is a theoretical line spread function (LSF) calculated at an intermediate focus for an exemplary lens according to the teachings of the invention having an apodized diffractive structure.
Figure 5A:
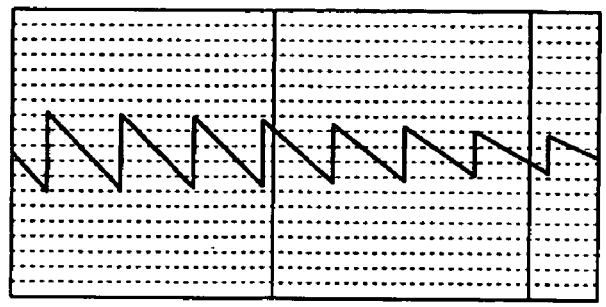
FIG. 5A shows the theoretical optical phase at the pupil of an apodized diffractive IOL lacking a frustrated diffractive structure according to the teachings of the invention, where the abscissa represents the square of the distance from the lens center, and the ordinate represents the optical phase.
Figure 5B:
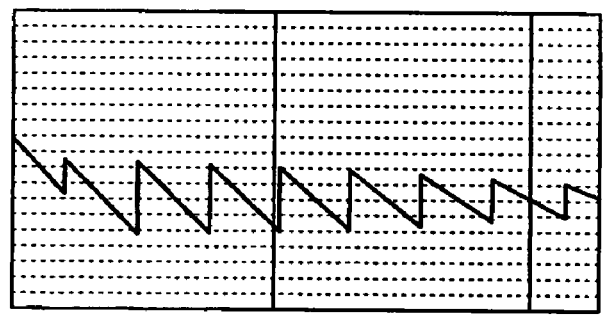
FIG. 5B shows the theoretical optical phase at the pupil of an apodized diffractive IOL in accordance with one embodiment of the invention, where the abscissa represents the square of the distance from the lens center, and the ordinate represents the optical phase.

By way of example, FIG. 4A depicts a calculated line spread function (LSF) profile, which corresponds to the intensity across the image of a line object, for an apodized diffractive lens having a conventional apodized diffractive structure in which all of the step heights are defined in accordance with the above Equation (4b) with a single b value (without a significant difference between the phase delays caused by the first two steps). FIG. 5A shows the theoretically calculated phase for such a lens across the lens pupil as a function of the square distance from the lens center. By way of comparison, FIG. 4B depicts the LSF profile of an apodized diffractive lens according to an embodiment of the invention having a diffractive structure whose steps heights are defined in accordance with Equations (4a) and (4b) (i.e., a lens exhibiting "frustrated diffraction") having a larger central zone diameter, and a smaller phase delay at the first step, than those of the conventional lens. And FIG. 5B shows the theoretically calculated optical phase for such a lens across the lens pupil as a function of the square of the distance from the lens center. Referring again to FIGS. 4A and 4B, both of the LSF profiles were calculated for a pupil diameter size of 3 mm. The LSF profile corresponding to the frustrated diffractive lens exhibits a distinct central line focus that is not present in the LSF corresponding to the conventional apodized diffractive lens, indicating that the frustrated diffractive lens directs a portion of the light energy to an intermediate location between the near and far foci and hence improves intermediate vision.

In some embodiments, the locations of one or more zone boundaries are altered relative to those defined by the above Eq. (1) so as to provide a frustrated diffraction, thereby directing a portion of the incident light to an intermediate location between the near and far foci. For example, the location of one or more zone boundaries can differ from those dictated by the above Eq. (1) by a factor in a range of about 20% to about 50%. In some embodiments, such configuration of the zone boundary locations is employed instead of adjusting the phase delays caused by the zone boundaries in order to achieve a frustrated diffraction—though in other embodiments the locations of the zone boundaries as well as their associated phase delays can be configured to obtain a frustrated diffraction. By way of example, the diameter of the central zone can be different, e.g., larger, than that defined by the above Eq. (1) such that the diffractive structure would direct some of the incident light to a location between the near and far foci. For example, the radius of the central zone can be larger than $\sqrt{\lambda f}$, e.g., by a factor in a range of about 20 to about 50 percent.

In some embodiments, the step heights associated with more than one zone boundary can be adjusted, e.g., in a manner discussed above, to cause the diffractive structure to direct a portion of the incident light to an intermediate location between the near and far foci.

Moreover, in some other embodiments, rather than adjusting the height of the step separating the central zone from its neighboring zone, one or more step heights associated with other zone boundaries are configured, e.g., in a manner discussed above, such that the diffractive structure would direct a portion of the incident light to an intermediate location between the near and far foci. For example, the diffraction can be "frustrated" at one or more peripheral zones.

Figure 6:
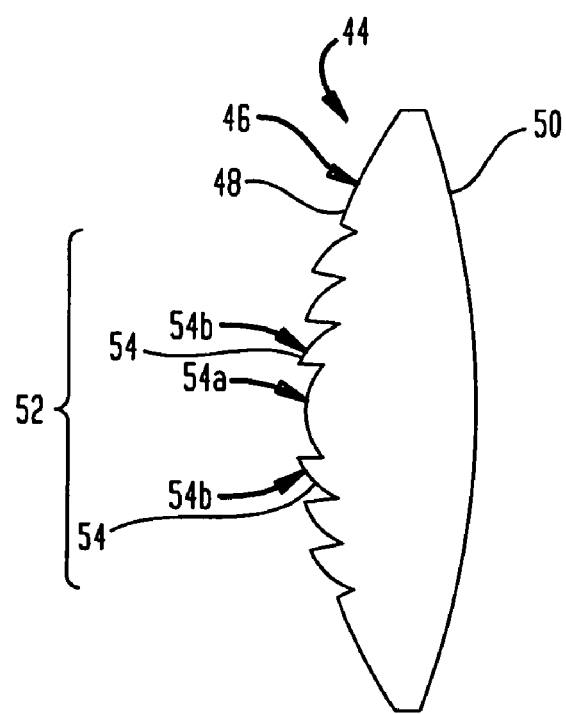
FIG. 6 is a schematic side view of a diffractive IOL according to one embodiment of the invention comprising a diffractive structure having a central diffractive region with a surface curvature that is different from that of an adjacent zone so that the diffractive structure would direct a portion of the incident light to an intermediate focus.

In some other embodiments, the surface curvature of at least one diffraction zone is different from that of at least one adjacent diffraction zone such that the diffractive structure would direct a portion of the incident light to an intermediate location between the near and far foci. By way of example, FIG. 6 schematically depicts an exemplary IOL 44 in accordance with such an embodiment that includes an optic 46 having an anterior optical surface 48 and a posterior optical surface 50. The IOL further includes a diffractive structure 52 disposed on a portion of the anterior surface. The optic 46 provides a far-focus optical power, e.g., in a range of about 6 D to about 34 D, and a near-focus add power, e.g., in a range of about 2 D to about 4 D. The diffractive structure 52 includes a plurality of diffraction zones 54 that are separated from one another by a plurality of steps, which can be uniform, apodized (either in a conventional manner or in a manner according to the teachings of the invention). In this exemplary embodiment, the diffractive structure is characterized by a plurality of substantially uniform step heights.

In this embodiment, the surface curvature of the central diffraction zone (i.e., zone 54a) is different (it is steeper in this case) from that of its adjacent zone (i.e., the zone 54b) such that the diffractive structure directs a portion of the incident radiation to an intermediate location between the near and far foci. By way of example, the difference between the surface curvatures of the two diffractive zones can be, e.g., in a range of about 10% to about 50%, for example, about 10%. Although in this embodiment, the surface curvatures of the central diffraction zone and that of its adjacent zone are configured to direct a portion of the incident light energy to the intermediate location, in alternative embodiments, other diffraction zones can be configured in this manner to provide an intermediate focus. Further, in some embodiments, the surface curvatures of more than two diffraction zones can be adapted, e.g., in a manner discussed above, to direct light to the intermediate location.

Figure 7:
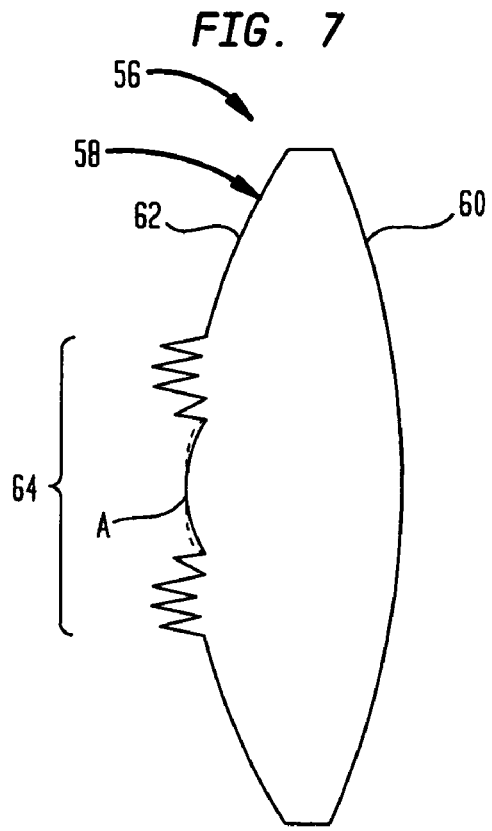
FIG. 7 is a schematic side view of a diffractive IOL according to another embodiment of the invention comprising a diffractive structure having a central zone that exhibits an aspheric surface profile.

In some embodiments, the surface of at least one diffraction zone exhibits an asphericity designed to cause the diffractive structure to send a portion of the incident light energy to the intermediate location. By way of example, FIG. 7 schematically depicts an IOL 56 comprising an optic 58 having a posterior optical surface 60 and an anterior optical surface 62 on which a diffractive structure 64 is disposed. Similar to the previous embodiments, the diffractive structure 64 is formed of a plurality of diffraction zones separated from one another by a plurality of steps. While in some cases (e.g., in this exemplary embodiment), the steps are configured to cause frustrated diffraction, in other embodiments the steps can be substantially uniform or be apodized in a conventional manner. The anterior surface 62 is characterized by a substantially spherical base profile. The surface profile of the central diffraction zone (zone A), however, exhibits an asphericity characterized, for example, by a conic constant in a range of about −10 to about −1000 (e.g., in a range of about −10 to about −100), so as to cause the diffractive structure to divert a portion of the incident light energy to the intermediate location.

In some embodiments, the surface profiles of a plurality of diffraction zones (the surface profiles between the zone boundaries) exhibit selected asphericities, e.g., similar to those discussed above, so as to direct light to the intermediate location. This corresponds to creating deviations from the straight lines for the sawtooth-like profiles shown in FIG. 5B.

Figure 8:
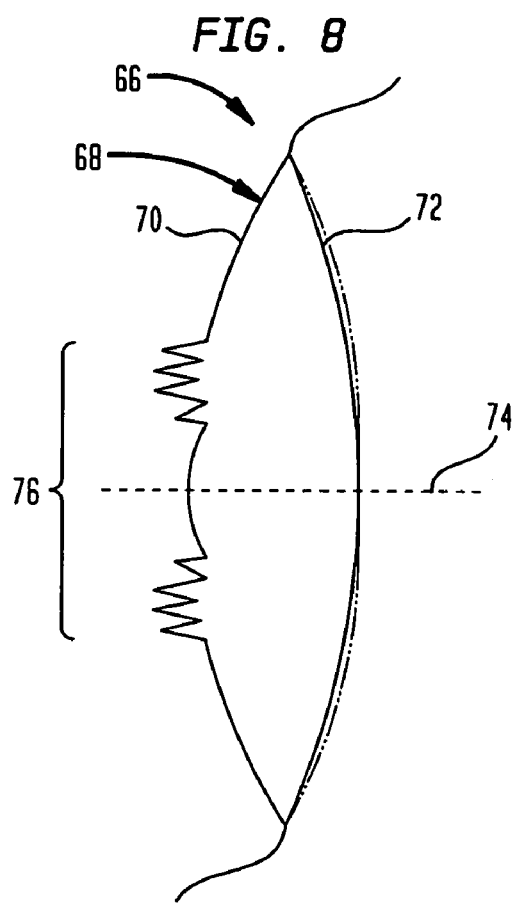
FIG. 8 is a schematic side view of a diffractive IOL according to another embodiment of the invention having an anterior surface on which a diffractive structure in accordance with the teachings of the invention is disposed and a posterior surface that can exhibit an aspheric, or in some cases, a toric base profile.

In some embodiments, the base profile of at least one of the IOL's optical surfaces exhibits a selected degree of asphericity or toricity so as to provide improved vision quality. For example, FIG. 8 schematically depicts an IOL 66 according to another embodiment of the invention that includes an optic 68 having an anterior optical surface 70 and a posterior optical surface 72 disposed about an optical axis 74. A frustrated diffractive structure 76 according to the teachings of the invention is disposed on the anterior surface. Further, the posterior surface includes a profile that is substantially coincident with a spherical profile (shown by dashed lines) at small distances from the optical axis and exhibits an increasing deviation from that spherical profile as a function of increasing radial distance from the optical axis. In some embodiments, this deviation can impart a selected degree of asphericity to the posterior surface, e.g., one characterized by a conic constant in a range of about −10 to about −1000 (e.g., in a range of about −10 to about −100), so as to provide improved vision quality. In some other embodiments, the base profile of the surface on which the frustrated diffractive structure is disposed (e.g., the anterior optical surface 20 in this case) can exhibit a selected degree of asphericity so as to enhance vision quality. Further, in other embodiments, one or more surfaces of an IOL having a frustrated diffractive structure, such as the above IOL 66, can exhibit a selected degree of toricity for enhanced vision quality. For example, the anterior and/or the posterior surfaces 70 or 72 of the IOL 66 can have a toric base profile.

In some embodiments, the frustrated diffractive IOL can be formed of a material that can provide some filtering of the blue light. By way of example, the IOL can be formed of Acrysof Natural material. By way of further example, U.S. Pat. No. 5,470,932, herein incorporated by reference, discloses polymerizable yellow dyes that can be utilized to block or lower the intensity of blue light transmitted through the IOL.

In the above embodiments, various ways of providing a frustrated diffractive lens are discussed. It should be understood each of the structural features utilized in the above embodiments for generating an intermediate focus can be employed individually, or in combination with one or more other features. For example, in some embodiments, in addition to configuring the step height separating the central zone from its adjacent zone to generate an intermediate focus, the curvature of the central zone can also be adjusted in a manner discussed above so as to direct a portion of incident light to the intermediate focus.

The various lenses discussed above can be fabricated by employing manufacturing techniques known in the art.

Those having ordinary skill in the art will appreciate that various changes can be made to the above embodiments without departing from the scope of the invention.

What is claimed is:

1. An ophthalmic lens, comprising
an optic having an anterior surface and a posterior surface,
a diffractive structure comprising a plurality of diffractive zones disposed on at least one of said surfaces, each zone being separated from an adjacent zone by a zone boundary,
said optic providing a far focus corresponding to a zeroth diffraction order of said diffractive zones and a near focus corresponding to a $1^{st}$ diffraction order of said diffractive zones,
wherein said zone boundaries are characterized by a plurality of non-uniform step heights generating non-uniform phase delays adapted to direct a portion of incident light to a location between said near and far foci so as to enhance intermediate vision.

2. The lens of claim 1, wherein said non-uniform step heights comprise at least two consecutive steps each imparting a phase delay to incident light such that a difference between the phase delays associated with said consecutive steps for at least one wavelength of the incident light is greater than about $\frac{1}{20}$ wavelength.

3. The lens of claim 2, wherein said optic provides a far-focus optical power in a range of about 6 D to about 34 D.

4. The lens of claim 2, wherein said optic provides a near-focus optical power corresponding to an add power in a range of about 2 D to about 4 D.

5. The lens of claim 1, wherein said diffractive zones are surrounded by a portion of the respective surface that lacks diffractive elements.

6. An ophthalmic lens, comprising
an optic having an anterior surface and a posterior surface, said optic providing a far-focus optical power; and
a diffractive structure comprising a plurality of diffractive zones disposed on at least one of said surfaces for providing a near-focus optical power,
wherein at least two of said diffractive zones exhibit sufficiently different surface curvatures so as to cause a portion of light incident on said optic to be directed to an intermediate location between said near and far foci for enhancing intermediate vision and wherein a difference in the curvatures of said at least two diffractive zones is in a range of about 10% to about 50%.

7. An ophthalmic lens, comprising:
an optic having an anterior surface and a posterior surface, said optic providing a far-focus optical power; and
a diffractive structure comprising a plurality of diffractive zones disposed on at least one of said surfaces for providing a near-focus optical power, wherein:
at least two of said diffractive zones exhibit sufficiently different surface curvatures so as to cause a portion of light incident on said optic to be directed to an intermediate location between said near and far foci for enhancing intermediate vision;
a difference in the curvatures of said at least two diffractive zones is in a range of about 10% to about 50%; and
said at least two diffractive zones comprise two adjacent zones.

8. An ophthalmic lens, comprising
an optic having an anterior surface and a posterior surface, said optic providing a far-focus optical power; and
a diffractive structure comprising a plurality of diffractive zones disposed on at least one of said surfaces for providing a near-focus optical power,
wherein at least two of said diffractive zones exhibit sufficiently different surface curvatures so as to cause a portion of light incident on said optic to be directed to an intermediate location between said near and far foci for enhancing intermediate vision, and wherein said near-focus optical power corresponds to an add power in a range of about 2 D to about 4 D.

9. An ophthalmic lens, comprising
an optic having an anterior surface and a posterior surface, said optic providing a far focus,
a diffractive structure comprising a plurality of diffractive zones disposed on at least one of said surfaces for providing a near focus,
wherein a surface of at least one of said diffractive zones exhibits an asphericity such that said diffractive structure directs at least a portion of incident light to an intermediate location between said near and far foci, wherein said asphericity is characterized by a conic constant in a range of about −10 to about −1000.

10. The lens of claim 9, wherein said ophthalmic lens comprises an IOL.

11. An ophthalmic lens, comprising
an optic having an anterior surface and a posterior surface, said optic providing a far focus,
a diffractive structure comprising a plurality of diffractive zones disposed on at least one of said surfaces for providing a near focus, wherein said near focus is characterized by an add power in a range of about 2 D to about 4 D,
wherein a surface of at least one of said diffractive zones exhibits an asphericity such that said diffractive structure directs at least a portion of incident light to an intermediate location between said near and far foci.

12. The lens of claim 11, wherein said ophthalmic lens comprises an IOL.

13. An ophthalmic lens, comprising
an optic having an anterior optical surface and a posterior optical surface, said optic providing a far focus,
a plurality of annular diffractive zones disposed on one of said surfaces about an optical axis of said optic so as to provide a near focus,
wherein at least one of said zones (i) has a boundary with a radial location defined by the following relation:

$$r_i^2 = r_0^2 + 2i\lambda f$$

wherein
i denotes the zone number (i=0 denotes the central zone),
$\lambda$ denotes a design wavelength,
f denotes a focal length of the near focus, and
$r_0$ denotes the radius of the central zone, and
wherein at least another zone has a boundary with a radial location that differs sufficiently from that defined by the above relation for a putative respective zone so as to direct a portion of incident light to an intermediate location between said far and near foci.

14. The lens of claim 13, wherein the radial location of said at least another zone differs from that defined by said relation by a factor in a range of about 20% to about 50%.

15. The lens of claim 13, wherein $\lambda$ is in a range of about 400 nm to about 700 nm.

16. The lens of claim 13, wherein said near focus corresponds to an add power in a range of about 2 D to about 4 D.

17. An ophthalmic lens, comprising
an optic having an anterior optical surface and a posterior optical surface, said optic providing a far focus,
a plurality of diffractive zones disposed on at least one of said surfaces to provide a near focus,
wherein said zones comprise a central zone having a radius that is sufficiently different from $\sqrt{\lambda f}$, where $\lambda$ denotes a design wavelength and f denotes a focal length of the near focus, such that at least a portion of incident light is directed to an intermediate location between said near and far foci.

18. The lens of claim 17, wherein $\lambda$ is in a range of about 400 nm to about 700 nm.

19. The lens of claim 17, wherein said near focus corresponds to an add power in a range of about 2 D to about 4 D.

* * * * *